(12) United States Patent
Feklistov et al.

(10) Patent No.: US 9,060,846 B2
(45) Date of Patent: *Jun. 23, 2015

(54) OPHTHALMIC LASER SYSTEM

(71) Applicant: ELLEX MEDICAL PTY LTD, Adelaide (AU)

(72) Inventors: Dmitri Feklistov, Adelaide (AU); Malcolm Plunkett, Adelaide (AU)

(73) Assignee: Ellex Medical Pty Ltd (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/601,177

(22) Filed: Jan. 20, 2015

(65) Prior Publication Data

US 2015/0141973 A1    May 21, 2015

Related U.S. Application Data

(60) Continuation of application No. 14/529,861, filed on Oct. 31, 2014, which is a continuation of application No. 14/148,683, filed on Jan. 6, 2014, now Pat. No. 8,876,808, which is a division of application No. 10/847,062, filed on May 17, 2004, which is a continuation-in-part of application No. PCT/AU03/01224, filed on Sep. 18, 2003.

(30) Foreign Application Priority Data

Sep. 18, 2002    (AU) ................................ 2002951467

(51) Int. Cl.
  *A61F 9/008*    (2006.01)

(52) U.S. Cl.
  CPC .............. *A61F 9/008* (2013.01); *A61F 9/00821* (2013.01); *A61F 9/00823* (2013.01); *A61F 9/0084* (2013.01); *A61F 2009/00868* (2013.01);

(Continued)

(58) Field of Classification Search
  USPC .......................................................... 606/4–6
  See application file for complete search history.

(56) References Cited

U.S. PATENT DOCUMENTS

| 4,276,518 A | 6/1981 | Ferguson |
| 4,309,998 A | 1/1982 | Aron nee Rosa et al. |
| 4,507,773 A | 3/1985 | McCann et al. |

(Continued)

FOREIGN PATENT DOCUMENTS

| EP | 1 086 674 A1 | 3/2001 |
| EP | 1 184 947 A1 | 3/2002 |

(Continued)

OTHER PUBLICATIONS

U.S. Appl. No. 10/847,062, Advisory Action and Examiner-Initiated Interview Summary mailed Dec. 31, 2014.

(Continued)

*Primary Examiner* — William Thomson
*Assistant Examiner* — Jeffrey Lipitz
(74) *Attorney, Agent, or Firm* — Alston & Bird LLP (57) ABSTRACT

An ophthalmic laser system generating a first beam at a wavelength suitable for performing selective laser trabeculoplasty and selectively generating a second beam at a wavelength suitable for performing secondary cataract surgery procedures. The laser system is able to select between directing the first beam or the second beam to the eye of a patient. The first beam is suitably generated at 1064 nm from a Nd:YAG laser and the second beam is frequency doubled to 532 nm in a KTP doubling crystal.

19 Claims, 5 Drawing Sheets

(52) U.S. Cl.
CPC ............... *A61F 2009/00887* (2013.01); *A61F 2009/00891* (2013.01)

(56) References Cited

U.S. PATENT DOCUMENTS

| | | | |
|---|---|---|---|
| 4,520,816 | A | 6/1985 | Schachar et al. |
| 4,530,600 | A | 7/1985 | Lopez |
| 4,588,262 | A | 5/1986 | Nelson |
| 4,648,892 | A | 3/1987 | Kittrell et al. |
| 4,732,460 | A | 3/1988 | Kele et al. |
| 5,434,667 | A | 7/1995 | Hutchins et al. |
| 5,549,596 | A | 8/1996 | Latina |
| 6,066,127 | A | 5/2000 | Abe |
| 6,325,792 | B1 | 12/2001 | Swinger et al. |
| 6,932,807 | B1 | 8/2005 | Tomita et al. |
| 8,876,808 | B2 | 11/2014 | Feklistov et al. |
| 2003/0187325 | A1 | 10/2003 | Meister et al. |
| 2004/0125834 | A1 | 7/2004 | Spierkermann et al. |
| 2004/0215175 | A1 | 10/2004 | Feklistov et al. |

FOREIGN PATENT DOCUMENTS

| | | |
|---|---|---|
| JP | 62-016253 A | 1/1987 |
| JP | 11-104145 A | 4/1999 |
| JP | 2001-161739 A | 6/2001 |
| WO | WO 95/24671 A1 | 9/1995 |
| WO | WO 02/15808 A | 2/2002 |
| WO | WO 2004/027487 A1 | 4/2004 |

OTHER PUBLICATIONS

"Paragon Laser Service Manual", Lynton Lasers Limited, Manchester, UK, Issue 3, pp. 3-1-3-21, (1996,).

*Complaint, LightMed Corp. v Ellex Med. Pty. Ltd.*, No. 3:13-cv-03933-MEJ (N.D. Cal. Aug. 23, 2013), 51 pages.

Decision on Motion to Dismiss, *LightMed Corp. v Ellex Med. Pty. Ltd.*, Case No. 2:13-cv-09205-PSG-PLA, (C.D. Cal. May 20, 2014), 21 pages.

EPO Application No. 03797087.8, European Examination Report, dated Mar. 10, 2008.

PCT International Preliminary Examination Report for application PCT/AU2003/001224 completed on Apr. 30, 2004.

PCT International Search Report for Application PCT/AU2003/001224 mailed Oct. 16, 2003.

U.S. Appl. No. 10/847,062, Declaration of Mark Horsburgh, 15 pages, submitted Mar. 12, 2010.

U.S. Appl. No. 10/847,062, Declaration of Mark Horsburgh, 2 pages, submitted Dec. 18, 2014.

U.S. Appl. No. 10/847,062, Declaration of Victor Previn, 3 pages, submitted Apr. 10, 2014.

U.S. Appl. No. 10/847,062, Declaration of Victor Previn, 4 pages, submitted Dec. 18, 2014.

U.S. Appl. No. 10/847,062, Final Office Action mailed Aug. 18, 2014.

U.S. Appl. No. 10/847,062, Non-Final Office Action mailed Jan. 14, 2014.

U.S. Appl. No. 14/148,683, Notice of Allowance and Examiner-Initiated Interview Summary mailed Jul. 14, 2014.

U.S. Appl. No. 14/148,683, Requirement for Restriction/Election mailed May 30, 2014.

U.S. Appl. No. 10/847,062, Advisory Action Before the Filing of an Appeal Brief, mailed Mar. 20, 2009.

U.S. Appl. No. 10/847,062, Advisory Action Before the Filing of an Appeal Brief, mailed May 3, 2010.

U.S. Appl. No. 10/847,062, Final Office Action, mailed Jan. 2, 2009.

U.S. Appl. No. 10/847,062, Final Office Action, mailed Jan. 14, 2010.

U.S. Appl. No. 10/847,062, Non-Final Office Action, mailed Apr. 7, 2008.

U.S. Appl. No. 10/847,062, Non-Final Office Action, mailed Jun. 10, 2009.

OPHTHALMIC LASER SYSTEM

CROSS-REFERENCE TO RELATED APPLICATIONS

The present application is a continuation of U.S. application Ser. No. 14/529,861 filed Oct. 31, 2014, which is a continuation of U.S. application Ser. No. 14/148,683 filed Jan. 6, 2014, which is now U.S. Pat. No. 8,876,808 issued Nov. 4, 2014, which is a divisional of U.S. application Ser. No. 10/847,062 filed May 17, 2004, which is a continuation-in-part of PCT/AU2003/001224 filed Sep. 18, 2003, which claims priority to Australian application no. 2002951467 filed Sep. 18, 2002.

FIELD OF THE INVENTION

This invention relates to a treatment laser instrument designed for use by ophthalmologists for performing selective laser trabeculoplasty (for treating glaucoma) procedures and secondary cataract surgery procedures. In particular, the invention relates to an ophthalmic laser system that can operate effectively in both the infrared region (for secondary cataract treatment) and other regions, such as the green region (for glaucoma treatment

BACKGROUND TO THE INVENTION

Glaucoma (abnormal intra-ocular pressure) is a major eye problem that leads to blindness in a significant percentage of the world population. Glaucoma is the most common cause of blindness in the world today. The established technique for treating glaucoma is drug based. Alternative treatment modalities have been sought to avoid the side effects and non-specificity associated with drug based treatments. Over the past few years a technique known as selective laser trabeculoplasty (SLT) has been invented by Latina. The technique is described in U.S. Pat. No. 5,549,596, assigned to The General Hospital Corporation. Latina describes the use of a frequency doubled Nd:YAG laser for the SLT procedure.

SLT is an improvement over a previously used technique referred to as argon laser trabeculoplasty (ALT). ALT uses a thermal effect to coagulate loose trabecular meshwork cells believed to be present in patients with glaucoma. Because an Argon laser is essentially CW (if pulsed, the pulse duration is long compared to thermal transfer mechanisms) there is significant heat transfer into surrounding tissue. This results in damage to otherwise healthy cells. It has been found that the ALT process can only be used once or twice before collateral damage prevents any further benefit from ALT treatment.

In contrast, SLT utilizes a pulsed laser (the pulse duration is short compared to thermal effects) so there is minimal heat transfer to surrounding tissue. SLT has been found to be repeatable, unlike the ALT process.

A detailed discussion of the SLT modality and a comparison with ALT is found in Ocular Surgery News published 1 Mar. 2000.

Another very common ophthalmic treatment is secondary cataract surgery. The most effective laser for secondary cataract surgery is a Nd:YAG laser operating at 1064 nm. These lasers are typically referred to as photodisruptors as they act by non-thermal mechanisms to cut tissue. A typical ophthalmic laser system consists of the laser head and a beam delivery system coupled to a conventional slit lamp assembly. A typical laser system for secondary cataract surgery is described in U.S. Pat. No. 6,325,792.

At present, two separate laser systems are necessary to perform the procedures for treating the two most common eye problems.

An attempt to address the problem of requiring multiple lasers for different treatment modalities has been described in U.S. Pat. No. 6,066,127. This patent describes a system for changing the laser cavity between a pulsed configuration and a continuous wave configuration by introducing a movable intracavity element. This approach is problematic because it is extremely difficult to maintain optimum alignment of the laser cavity with a movable intracavity element.

A better solution is required.

SUMMARY OF THE INVENTION

In one form, although it need not be the only or indeed the broadest form, the invention resides in an ophthalmic laser system comprising:

a laser module producing a beam of short pulses of radiation with high energy density at a first wavelength;

a first beam path incorporating an attenuator, beam shaping optics, and means for directing the beam at said first wavelength to an eye of a patient;

a second beam path incorporating a frequency conversion module that converts the beam at the first wavelength to a beam at a second wavelength, an attenuator, and means for directing the beam at said second wavelength to the eye of the patient; and extracavity deflecting means for selectively deflecting the beam at said first wavelength into the second beam path, said means being operable between a first position in which the beam at said first wavelength follows the first beam path and a second position in which the beam at said first wavelength is deflected to said second beam path.

Preferably the beam at said first wavelength is a 1064 nm beam produced by a Nd:YAG laser, and said beam at said second wavelength is frequency-doubled to 532 nm. The beam is suitably doubled by a KTP doubling crystal or similar frequency doubling device.

Preferably the extracavity deflecting means comprises a half wave plate and polarizer. The half wave plate is suitably remotely operable, such as by a servo motor or solenoid.

BRIEF DESCRIPTION OF THE DRAWINGS

To assist in understanding the invention, preferred embodiments will be described with reference to the following figures in which.

DETAILED DESCRIPTION

Figure 1:
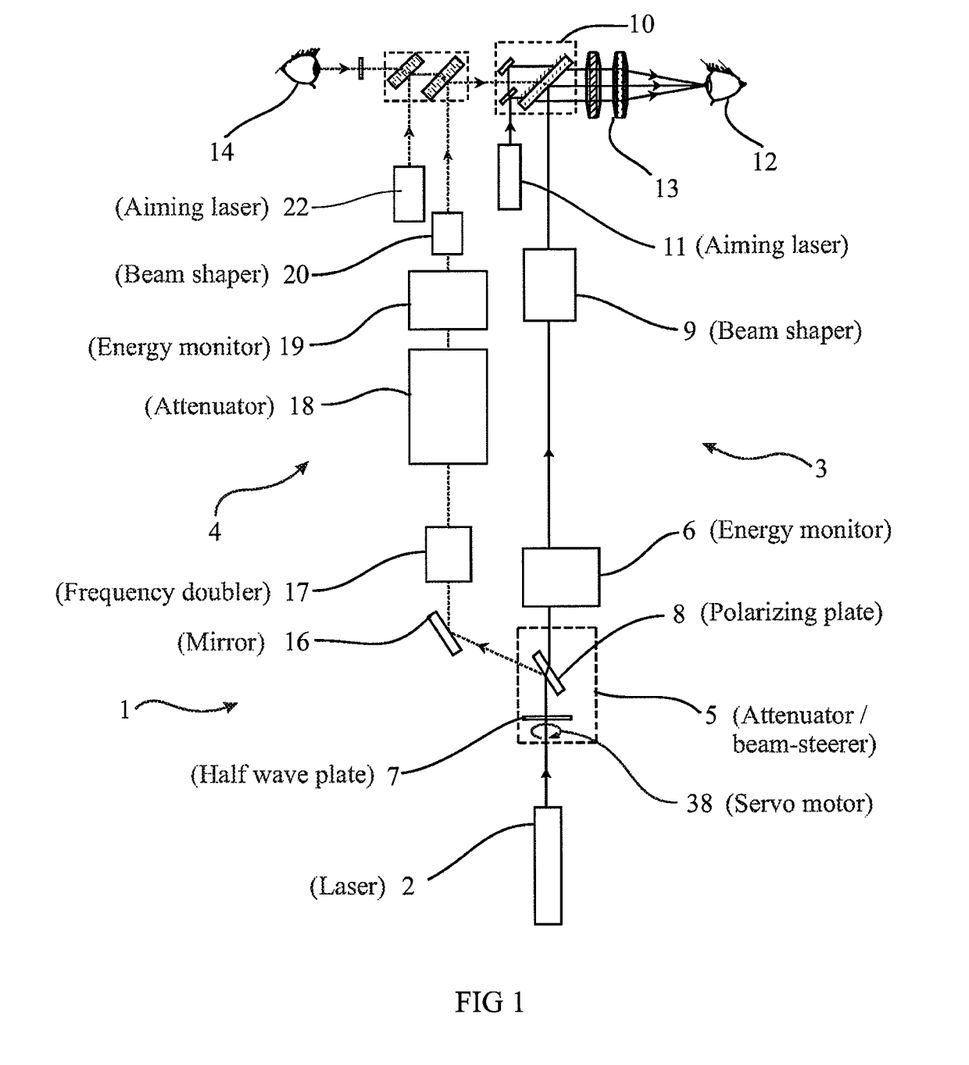
FIG. 1 shows a general schematic view of an ophthalmic laser system.

Referring to FIG. 1, there is shown an embodiment of an ophthalmic laser system 1 useful for treating glaucoma and secondary cataracts. The system is comprised of a laser module 2, a photodisruptor optical system 3 and SLT optical system 4, as shown separately in FIGS. 2 and 3.

The ophthalmic laser system 1 of the present invention combines the photodisruptor optical system 3 and SLT optical system 4 into one integral unit, which uses a single laser module 2. The laser module 2 is a Q switched Nd:YAG laser operating in the infrared spectrum. The laser emits a beam at 1064 nm wavelength, having a pulse width of less than 5 nsec. Other laser modules (such as Nd:YLF, Yb:YAG, etc) will also be suitable as will be readily apparent to persons skilled in the art.

Figure 2:
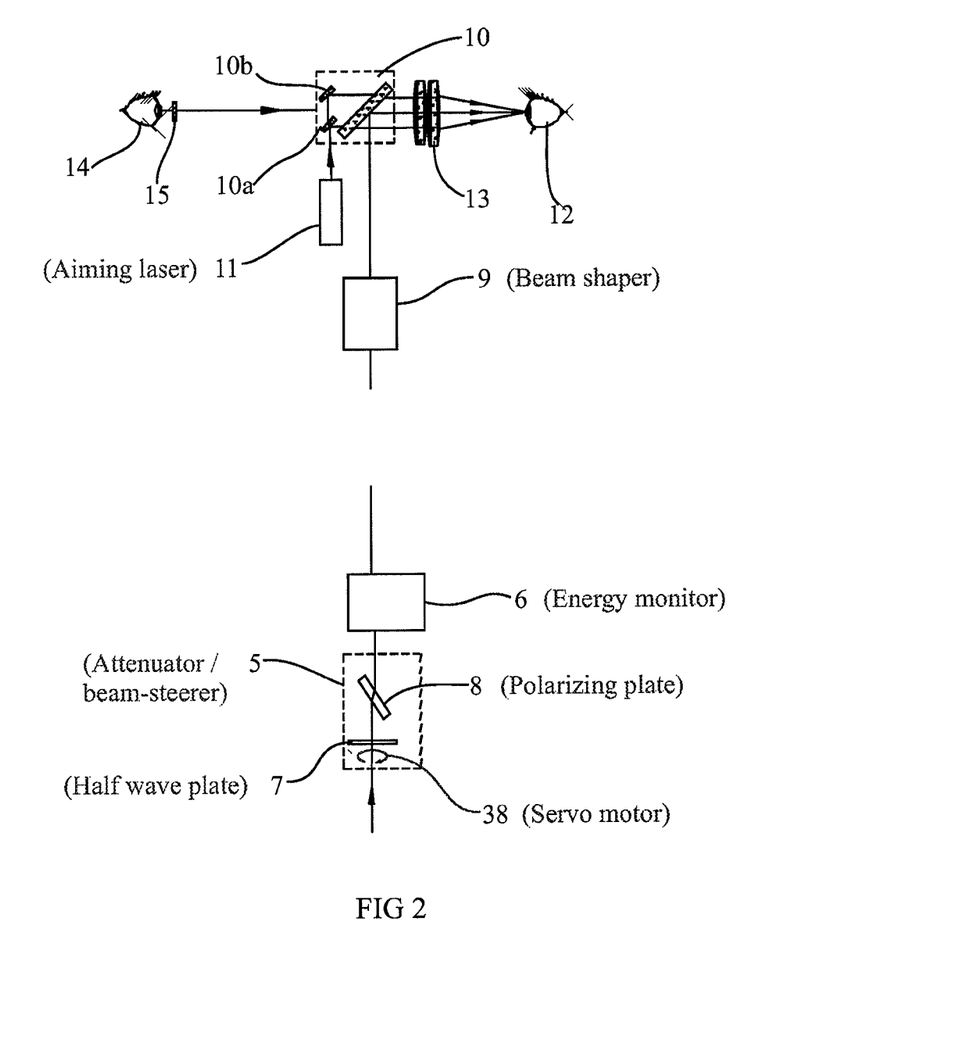
FIG. 2 shows a schematic side view of the photodisruptor optical system of the ophthalmic laser system in FIG. 1.

Referring now to FIG. 1 and FIG. 2, a pulsed beam from the laser module 2 is attenuated at attenuator/beam steering module 5. An energy monitor system 6 measures the energy in each pulse. For the photodisruptor optical system the desired energy density is 0.3-10 mj in an 8-10 μm spot. A half wave plate 7 within the attenuator/beam steering module 5 is adjusted to regulate the intensity of the pulsed beam in the photodisruptor optical system 3. A polarizing plate 8 may deflect the pulsed beam to the SLT optical system 4 depending on the orientation of the half wave plate 7. The function of the attenuator/beam steering module 5 will be described in more detail later.

Beam shaping optical module 9 expands the pulsed beam before it travels up to the folding mirror module 10. The expanded beam is then focused by objective lens 13 to produce the 8-10 μm beam waist at the treatment site which is required to produce photodisruption. An aiming laser module 11 provides a continuous, visible laser beam that is split into two beams and deflected by folding mirror module 10 to give a targeting reference for the treatment beam. These two aiming laser beams converge with the pulsed treatment beam at the target site in a patient's eye 12 via objective lens 13. An operator 14 views the patient's eye 12 through the folding mirror module 10. A safety filter 15 protects the eye of the operator. The folding mirrors 10a, 10b are positioned so that the viewing axis of the operator is not impeded. It will be appreciated by those skilled in the art that the mirrors may be replaced by prisms or other suitable beam steering optics.

Figure 3:
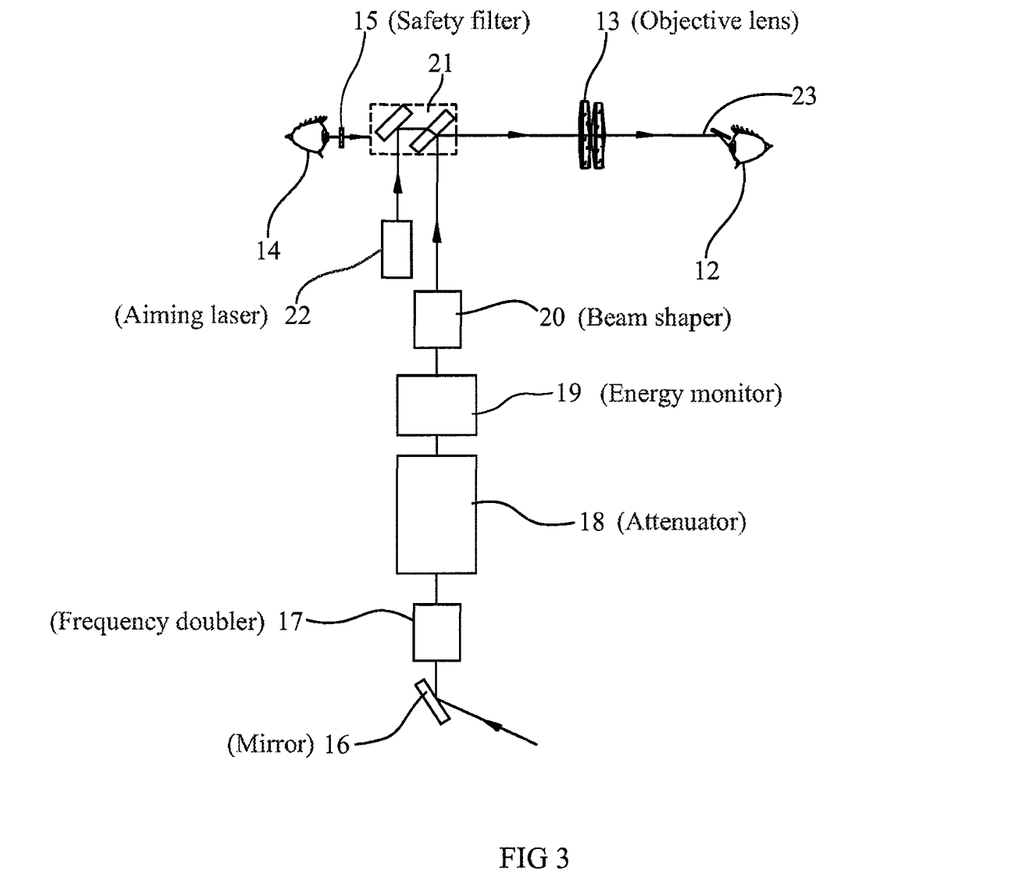
FIG. 3 shows a schematic view of the SLT optical system of the ophthalmic laser system in FIG. 1.

Referring to FIG. 3, the SLT optical system 4 comprises a mirror 16 that directs a deflected pulsed beam from the polarizing plate 8 in the attenuator/beam steering module 5 of FIG. 1 to the frequency conversion module, which is a frequency doubling module 17 in the preferred embodiment. To maximize frequency doubling efficiency the entire pulsed beam is deflected by attenuator/beamsteering module 5. The frequency doubling module 17 converts the output of the laser module to half the wavelength so that the output of the SLT optical system is in the visible spectrum. For the particular embodiment the Nd:YAG laser module operates in the near infrared at 1064 nm which is frequency doubled to 532 nm, which is in the green region of the visible spectrum. The green pulsed beam is effective in treating glaucoma in patients.

The pulsed green beam may be attenuated at the SLT attenuator 18 to regulate the energy in the pulsed green beam. An energy monitor system 19 measures the energy in each pulse. For the SLT process the desired energy density is 0.01-5 J/cm², as described by Latina.

Other wavelengths may be suitable for other ophthalmic applications in which case the frequency conversion module may triple or quadruple the fundamental frequency. In some applications it may even be desirable to use a tunable frequency conversion module, such as an optical parametric oscillator.

A beam shaping module 20 adjusts the beam profile to provide an even energy distribution at the treatment plane.

The green beam then travels to a second folding mirror module 21. A second aiming laser module 22 provides a single aiming laser beam which is deflected by the second folding mirror 21 and transmitted through folding mirror module 10 and objective lens 13, as shown in FIG. 1. The continuous visible laser aiming beam generated by the second aiming laser module 22 coincides with the green pulsed beam at the target site in a patient's eye 12 via objective lens 13 and contact lens 23. As mentioned earlier, the mirror could be replaced by prisms or other suitable optical elements.

Although two separate aiming laser modules 11, 22 are described, it will be appreciated that a single aiming laser module could be used with appropriate beam deflecting optics, such as a mirror, to direct the aiming laser beam through folding mirror module 10 for off-axis illumination or folding mirror module 21 for on-axis illumination.

The present invention provides an ophthalmic laser system for treating glaucoma and secondary cataract conditions, using a single laser source. The present invention integrates two known laser treatment techniques, SLT and photodisruptor, into one integrated system.

The method used to direct the laser beam from the laser module 2 to the photodisruptor optical system 3 or the SLT optical system 4 will now be described in detail. Referring to FIG. 1, the attenuator/beam steering module 5 first receives a pulsed and linearly polarized beam from laser module 2 at half wave plate 7. The pulsed beam passes through the half wave plate to the polarizing plate 8.

The orientation of the half wave plate 7 determines the amount of the pulsed beam that is passed through the polarizing plate 8 into the photodisruptor optical system 3. The orientation of the half wave plate 7 can be adjusted by motorized means so that the polarization angle of the component of the resulting beam which coincides with the transmission characteristic of the polarizing plate 8 will be passed through to the beam shaping module 9. However, as the half wave plate 7 is rotated, the polarization of the beam is changed. Accordingly, only some portion of the beam will be transmitted.

In the photodisruptor mode for treating secondary cataracts, the half wave plate 7 is rotated to permit transmission of the required pulsed laser beam emitted from the laser module 2. If the SLT mode is required, the half wave plate 7 is oriented so that all the beam is reflected from the polarising plate 8 to the mirror 16 of the SLT optical system 4.

The ophthalmic laser system described above allows an operator to select the mode of treatment to be administered to a patient, simply by choosing one of two optical paths. A simple adjustment of the half wave plate 7 determines whether a SLT or a photodisruptor mode is chosen for treating glaucoma or secondary cataracts respectively. The adjustment of the half wave plate can be motorized so the selection of treatment modality may be by simple button selection.

It will be appreciated that the directing of the Nd:YAG laser beam into the photodisruptor module path or the SLT module path can be achieved by any suitable means (such as a mirror) but the use of a polarizing plate is preferred.

Figure 4:
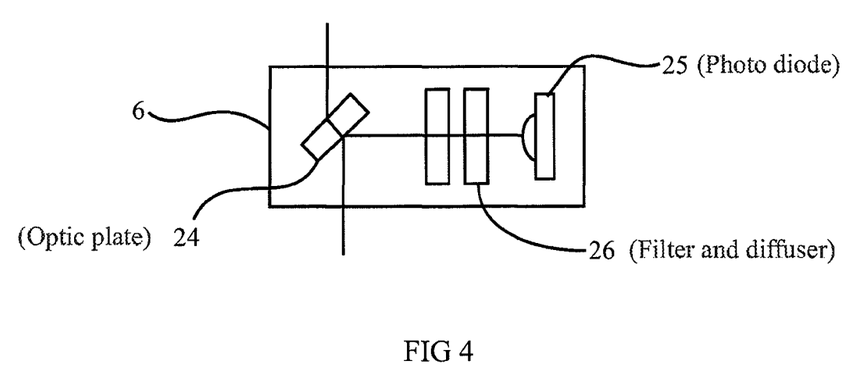
FIG. 4 shows a schematic view of the energy monitor system.

As mentioned above, each optical system includes an energy monitor system in the preferred embodiment. A schematic of the components of an energy monitor system is shown in FIG. 4. A small percentage of the beam is split by optic plate 24 towards a photodiode 25. A number of filters and diffusers 26 are positioned in of the photodiode 25.

Figure 5:
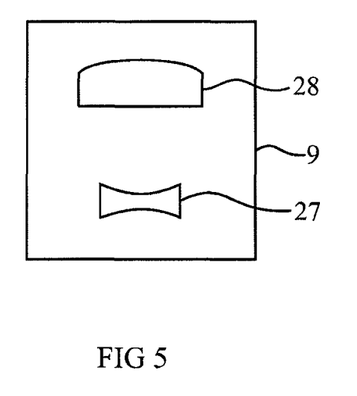
FIG. 5 shows a schematic of the beam-shaping module of the photodisruptor optical system.

As seen in FIG. 2, once the pulse beam is attenuated to the desired power, the beam is further conditioned by beam shaping optical module 9. The beam shaping optical module 9 is shown in more detail in FIG. 5. Lenses 27 and 28 form a beam expander which expands the 3 mm diameter beam from the laser module 2 by ten times. The expanded beam is reflected into the optical viewing path by the folding mirror 10 which uses a wavelength selective coating to avoid blocking of the viewing path. The beam from folding mirror 10 is then focused by objective lens 13 to produce the 8-10 µm beam waist at the treatment site which is required to produce photodisruption.

Figure 6:
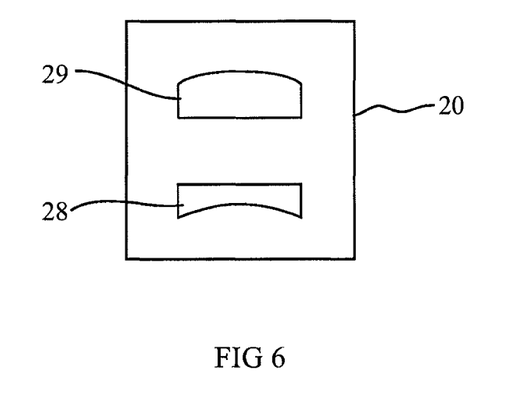
FIG. 6 shows a schematic of the beam-shaping module of the SLT optical system.

Referring to FIG. 6, the SLT beam is conditioned by beam shaping module 20 before the folding mirror module 21. The beam shaping module 20 consists of two lenses 28, 29 that form a beam expander that is designed to produce a well defined treatment spot with an even energy distribution.

Figure 7:
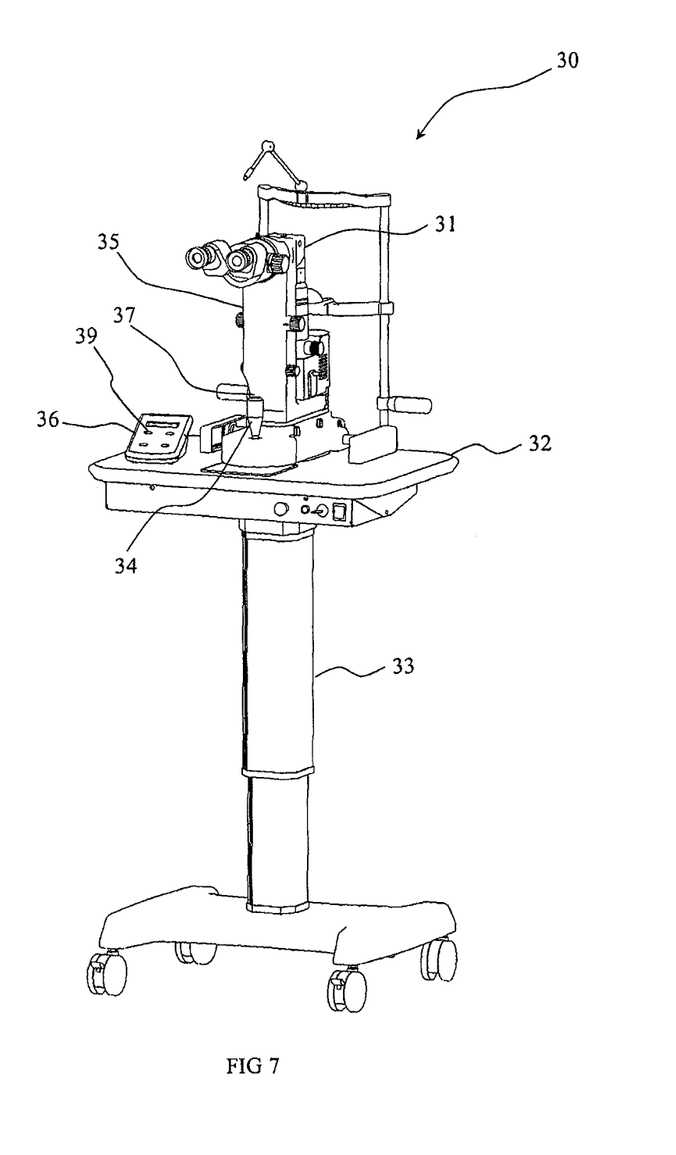
FIG. 7 shows an external view of an ophthalmic treatment device incorporating the ophthalmic laser system.

The invention is conveniently embodied in an ophthalmic treatment device of the type shown in FIG. 7. The treatment device 30 is of the conventional form having a slit lamp assembly 31 mounted on a table 32 which is in turn mounted on a height adjusting pedestal 33. The slit lamp assembly 31 is movable with respect to the table 32 + using joystick 34, in conventional manner. The ophthalmic laser system is mounted in the body 35 of the slit lamp assembly 31. This is achieved by using a compact laser cavity and careful placement of optical components.

The ophthalmic laser system is controlled by a control panel 36. The joy stick 34 may incorporate a fire button 37 to fire the laser, or alternatively a foot pedal (not shown) may be used.

The invention has been described with reference to one particular embodiment however, it should be noted that other embodiments are envisaged within the spirit and scope of the invention. For instance, one or two aiming lasers could be used, the photodisruptor or SLT beam path could be selected by a movable mirror, or the beam shaping optics could have a different configuration.

The invention claimed is:

1. A method of treating secondary cataract or glaucoma in a patient using an ophthalmic laser system comprising:
    a laser module comprising a Q-switched laser which operates to produce pulsed radiation at a first wavelength,
    a first beam path adapted to treating secondary cataract incorporating an attenuator, beam shaping optics, and directing optics for directing the beam of short pulses at the first wavelength to an eye of a patient with secondary cataract;
    a second beam path adapted to treating glaucoma by selective laser trabeculoplasty incorporating a frequency conversion module that converts the pulsed beam at the first wavelength to a pulsed beam at a second wavelength, an attenuator, and directing optics for directing the pulsed beam at the second wavelength to an eye of a patient with glaucoma; and
    beam steering optics for selectively deflecting the beam of short pulses at the first wavelength into the second beam path, the beam steering optics being operable between a first position in which the pulsed beam at the first wavelength is received by and follows the first beam path and a second position in which the pulsed beam at the first wavelength is deflected to, received by and follows the second beam path;
    the method comprising:
    operating the beam steering optics to select the first or second beam path depending on whether the patient has secondary cataract or glaucoma; and operating the laser system through the selected beam path to treat the patient.

2. An ophthalmic laser system for selective treatment of glaucoma and secondary cataract, the ophthalmic laser system comprising:
    a laser module comprising a Q-switched laser which operates to produce pulsed radiation at a first wavelength,
    a first beam path adapted to treating secondary cataract incorporating an attenuator, beam shaping optics, and directing optics for directing the beam of short pulses at the first wavelength to an eye of a patient with secondary cataract;
    a second beam path adapted to treating glaucoma by selective laser trabeculoplasty incorporating a frequency conversion module that converts the pulsed beam at the first wavelength to a pulsed beam at a second wavelength, an attenuator, and directing optics for directing the pulsed beam at the second wavelength to an eye of a patient with glaucoma; and
    beam steering optics for selectively deflecting the beam of short pulses at the first wavelength into the second beam path, the beam steering optics being operable between a first position in which the pulsed beam at the first wavelength is received by and follows the first beam path and a second position in which the pulsed beam at the first wavelength is deflected to, received by and follows the second beam path.

3. The ophthalmic laser system of claim 2, wherein the beam steering optics comprises a rotational half wave plate and polarizer, the half wave plate being rotationally operable between the first and second position.

4. The ophthalmic laser system of claim 3, wherein the rotational half wave plate and the polarizer serve as the attenuator in the first beam path, the rotational half wave plate being operable between first positions in which the pulsed beam at the first wavelength is received by and follows the first beam path at different intensities depending on the orientation of the waveplate and a second position in which substantially all the beam of short pulses at said first wavelength is deflected to be received and follow the second beam path.

5. The ophthalmic laser system of claim 2 further comprising a motor to rotate the half wave plate between the first position and the second position.

6. The ophthalmic laser system of claim 2 further comprising a remote control panel enabling selection between the first position and the second position.

7. The ophthalmic laser system of claim 2 wherein the laser module is a flashlamp pumped, solid state laser.

8. The ophthalmic laser system of claim 2 wherein the laser module is a Nd:YAG laser producing the beam at the first wavelength at a wavelength of 1064 nm, and the beam at the second wavelength is frequency-doubled to 532 nm.

9. The ophthalmic laser system of claim 2 wherein the beam shaping optics in the first beam path comprises a beam expander.

10. The ophthalmic laser system of claim 2 wherein the first beam path further incorporates an energy monitor system.

11. The ophthalmic laser system of claim 2 further comprising an aiming laser providing a targeting reference for the beam at the first wavelength.

12. The ophthalmic laser system of claim 2 wherein the frequency conversion module comprises a potassium titanyl phosphate (KTP) doubling crystal.

13. The ophthalmic laser system of claim 2 wherein the second beam path further incorporates an energy monitor system.

14. The ophthalmic laser system of claim 2 wherein the second beam path further incorporates beam shaping optics.

15. The ophthalmic laser system of claim 2 further comprising an aiming laser providing a targeting reference for the beam at the second wavelength.

16. The ophthalmic laser system of claim 2 mounted within a body of a slit lamp assembly.

17. The ophthalmic laser system of claim 2, wherein the optics for directing the pulsed beam at the first wave length comprises a mirror and the optics for directing the pulsed beam at the second wave length comprises a mirror.

18. The ophthalmic laser system of claim 2, which is adapted to produce 0.3-10 mJ in the eye of the patient with secondary cataract and 0.01-5 J/cm2 in the eye of the patient with glaucoma.

19. The ophthalmic laser system of claim 2, which is adapted to produce an 8-10 µm spot size in the eye of the patient with secondary cataract.

* * * * *